United States Patent
Kumar et al.

(10) Patent No.: US 6,410,282 B1
(45) Date of Patent: Jun. 25, 2002

(54) METHOD FOR ENHANCING LEVELS OF POLYUNSATURATED FATTY ACIDS IN THRAUSTOCHYTRID FUNGI

(75) Inventors: Seshagiri Raghu Kumar; Dorai Rajasingam Chandramohan; Ehrlich Desa, all of Goa (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/538,984

(22) Filed: Mar. 30, 2000

(51) Int. Cl.⁷ .................................................. C12P 7/64
(52) U.S. Cl. ........................................ 435/134; 435/244
(58) Field of Search ............................... 435/134, 135, 435/244

(56) References Cited

FOREIGN PATENT DOCUMENTS

WO          98/03671   *   1/1998

OTHER PUBLICATIONS

Shimada, et al., J. Ferment. Bioeng. (1996), 81(4), 299–303.*
Yadwad et al., Biotechnol. Bioeng. (1991), 38(8), 956–9.*

* cited by examiner

Primary Examiner—Irene Marx
(74) Attorney, Agent, or Firm—Foley & Lardner

(57) ABSTRACT

The invention relates to a method for enhancing levels of polyunsaturated fatty acid levels in thraustochytrid fungi, using media supplemented with polyvinyl pyrrolidone (PVP) to increase viscosity and which comprises: (a) providing a thraustochytrid fungus strain NIO-TH 21, corresponding to the species *Ulkenia radiata* Gaertner, being the culture with Accession No. AB22115 of the National Institute of Bioscience and Human-Technology, Japan; (b) inoculating the above said strain in a culture medium; (c) growing the culture for 2 days at a temperature ranging from 25 to 30° C.; (d) obtaining the cultures for use as innoculum using the above said medium to inoculate a medium with different concentrations of polyvinyl pyrrolidone (PVP); (e) growing the culture separately for 2 to 5 days at a temperature ranging from 25 to 30° C.; and (f) harvesting the cells from the above culture by centrifugation and extracting the enhanced amounts of docosahexaenoic acid (DHA) and eicosapentaenoic acids (EPA).

6 Claims, 2 Drawing Sheets

EPA in thraustochytrid culture NIO-TH 21

DHA in thraustochytrid strain NIO-TH 21

METHOD FOR ENHANCING LEVELS OF POLYUNSATURATED FATTY ACIDS IN THRAUSTOCHYTRID FUNGI

FIELD OF THE INVENTION

The present invention relates to a method for enhancing levels of polyunsaturated fatty acids in thraustochytrid fungi. The present invention particularly relates to a process for enhancement of the polyunsaturated fatty acids, docosahexaenoic acid and eicosapentaenoic acid in cells of microorganisms belonging to the group of fungi termed thraustochytrids, by growing the cells in a medium with increased viscosity. The cells thus enriched in the said polyunsaturated fatty acids (PUFAs) can then be utilized more successfully than cells that are not enriched in the PUFAs, in various beneficial applications that require polyunsaturated fatty acids, such as in animal feeds, human nutrition and extraction of the PUFAs for nutritional supplementation.

BACKGROUND OF THE INVENTION

Fatty acids are constituents of lipids, which are required by all living organisms for growth, survival and reproduction. Among the fatty acids, saturated fatty acids are those with a chemical structure in which the carbon atoms are connected to each other only by single bonds and contain no double bonds. Unsaturated fatty acids are those in which one or more of the carbon atoms are connected to each other by double bonds. Polyunsaturated fatty acids, termed as PUFAs hereafter, are those in which more than one such double bonds are found.

Among the PUFAs, two are considered extremely essential in the health of animals and human beings. These are the docosahexaenoic acid and eicosapentaenoic acid, termed DHA and EPA hereafter. The molecular structure of both DHA and EPA is such that the first double bond follows the third carbon atom from the methyl end of the fatty acid structure. Therefore, these are also called omega-3 PUFAs. DHA contains 22 carbon atoms, between which six double bonds are found. EPA contains 20 carbon atoms, between which five double bonds occur. Both DHA and EPA have been shown to be important for human health and in animal nutrition. In human health, DHA and EPA have been shown to be important in brain development in children, prevention of atherosclerosis, prevention of night blindness, neurological disorders and even for possible prevention of cancer (Bajpai, P. and P. K. Bajpai. 1993. Journal of Biotechnology 30: 161–183; Barclay, W. R. et al. 1994. Journal of Applied Phycology 6: 123–129; U.S. Pat. No. 9,428,913; Singh, A. and O. P. Ward. 1997. Advances in applied microbiology, 45: 271–312). These two omega-3 PUFAs have been shown to enhance growth and reproduction in crustacean animals, such as prawns, which are very important as aquaculture animals for human consumption (Harrison, K. E. 1990. Journal of Shellfish Research 9: 1–28). Incorporation of DHA and EPA in human and animal feeds is therefore considered important. DHA and EPA levels of thraustochytrid fungi can be enhanced beyond their natural levels by growing the cells in a medium with increased viscosity, as detailed in the present invention, and their cells can be of still better use as supplement to human nutrition and as feed for animals compared to presently known processes. Thraustochytrids can be cultivated on a large scale, using well established fermentation techniques. Cells thus obtained can be used as animal feeds, by suitably processing and preserving their cells, such as by spray-drying and freezing. The cell biomass, enhanced in the omega-3 fatty acids can also be harvested and DHA and EPA extracted in a pure form. These may be used to supplement human food that is poor in these essential omega-3 PUFAs.

One major source of EPA and DHA for human consumption is in the form of fish oil. However, fish oil has the disadvantage of an odour, which is disagreeable to many human consumers. Fish containing DHA and EPA are also highly seasonal and variable in their omega-3 PUFA contents. Besides, most of the fish oil is hydrogenated and the omega-3 PUFAs are destroyed. For these reasons, microorganisms containing EPA and DHA, which can be cultivated on a large scale are considered suitable for use in human nutrition and animal feeds (Bajpai, P. and P. K. Bajpai. 1993. Journal of Biotechnology 30: 161–183). Several single-celled plants, the algae, contain high levels of EPA and DHA and have been considered for the said purposes. References may be made to D. L. Alonso et al. (Alonso, D. L. et al., 1992. Aquaculture 102: 363–371). However, large scale cultivation of these plants in natural ponds often is subject to the problem of other microorganisms growing along with these plants. This may pose a health problem to human consumers. Growing them in pure cultures in fermentors is cost-intensive, since these plants require light and suitable photo reactors are very expensive to maintain and operate. Microorganisms can be easily cultivated on a large scale using cheap nutrients. Several groups of microorganisms contain high amounts of EPA and DHA. Such organisms can be used directly as feed, or the said PUFAs can be extracted from them for further use. Search for microorganisms containing high amounts of DHA and EPA has shown that thraustochytrid fungi contain some of the highest amounts of DHA and EPA. Thraustochytrids are already considered of commercial importance. Their cells are used in animal feeds or for extraction of PUFAs for commercial use (Singh, A. and O. P. Ward. 1997. Advances in applied Microbiology 45: 271–312). The Japanese Patent No. 9633263 (1996) describes a strain of a thraustochytrid for application in the food industry such as food-additives, nutritional supplements, as additives for infant milk formula, feedstuffs and drug additives. The strain contains at least 2% of dry wt as DHA. Another Japanese patent No. 980 3671 (1998) describes the production by fermentation of DHA and another PUFA, docosapentaenoic acid (DPA) from lipids of thraustochytrid fungi. U.S. Pat. No. 5,340,594 describes a process for production of whole-celled or extracted microbial products using thraustochytrid fungi with a high concentration of the omega-3 PUFAs. U.S. Pat. No. 5,340,742 discloses a process for growing the thraustochytrid fungi in defined media suitable for their growth. All the above patents relate to screening numerous thraustochytrid cultures, selecting the strain with the highest DHA and EPA content, prepare mutant strains of these and cultivate such strains under optimal culture conditions for commercial application.

The present invention aims to further increase the DHA and EPA levels in thraustochytrid fungi so that they will provide still higher commercial yields of the said PUFAs. Besides, the above mentioned prior art patents reject a large number of strains, which might have only moderate DHA and EPA concentrations. In the present invention, even strains with moderate amounts of DHA and EPA can be made to produce large amounts of these PUFAs by growing them in a medium with increased viscosity. Strains that naturally have high concentrations of DHA and EPA can be made to produce even more of these using the present process.

OBJECTS OF THE INVENTION

The main object of the present invention is to enhance the amounts of PUFAs in thraustochytrid fungi, which obviates the drawbacks as detailed above.

Another object of the invention is to make strains of thraustochytrids to produce higher amounts of DHA and EPA than they normally produce using optimal nutrient conditions.

Yet another object of the present invention is to enhance the levels of these fatty acids by growing the cultures of thraustochytrid fungi in a medium with increased viscosity.

SUMMARY OF THE INVENTION

To meet the above objects, the present invention provides a method for enhancing levels of polyunsaturated fatty acid levels in thraustochytrid fungi, using culture media supplemented with polyvinyl pyrrolidone (PVP) to increase viscosity.

DETAILED DESCRIPTION OF THE INVENTION

Accordingly, the present invention provides a method for enhancing levels of polyunsaturated fatty acid levels in thraustochytrid fungi, using culture media supplemented with polyvinyl pyrrolidone (PVP) to increase viscosity and which comprises: Step a: Providing a thraustochytrid fungus strain NIO-TH 21, corresponding to the species *Ulkenia radiata* Gaertner, being the culture with Accession No. AB22115 of the National Institute of Bioscience and Human-Technology, Japan; Step b: Inoculating the above said strain in a culture medium; Step c: Growing the culture for 2 days at a temperature ranging from 25 to 30° C.; Step d: Obtaining the cultures for use as inoculum using the above said medium to inoculate a medium with different concentrations of polyvinyl pyrrolidone (PVP); Step e: Growing the culture separately for 2 to 5 days at a temperature ranging from 25 to 30° C.; Step f: Harvesting the cells from the above culture by centrifugation and extracting the enhanced amounts of docosahexaenoic acid (DHA) and eicosapentaenoic acids (EPA).

In an embodiment of the present invention, the viscosity of the medium is increased by incorporating polyvinyl pyrrolidone (PVP) at concentrations ranging from 0.1 to 1.0%.

In yet another embodiment of the present invention, a process is provided to enhance the levels of the PUFAs in cells of thraustochytrid fungi.

In yet another embodiment of the present invention, the PUFAs that are enhanced are the DHA and EPA.

In yet another embodiment of the present invention, DHA and EPA are enhanced in cells of thraustochytrid fungi by growing the cultures in a medium with increased viscosity.

In yet another embodiment of the present invention, the increase in viscosity is provided by incorporating a substance that is not utilized as nutrients such as polyvinyl pyrrolidone (PVP) at concentrations ranging from 0.1 to 1.0%.

In still another embodiment, the culture medium used comprising peptone in the range of 0.5% Wt. to 1.5% Wt., preferably, 1.5% Wt.; Yeast extract in the range of 0.01% Wt. to 0.1% Wt., preferably, 0.1% Wt.; Glucose in the range of 0.01% to 1.0% Wt., preferably, 1.0% Wt.; and Sea water of 100 ml.

In yet another embodiment, the culture medium comprises 1.5% peptone; 0.1% yeast extract; 1.0% glucose; 0.5% polyvinyl pyrrolidone and 100 ml sea water.

According to the present invention, culture of a candidate species of the thraustochytrid fungus, which contains the omega-3 PUFAs DHA and EPA is first inoculated into a liquid nutrient medium. Strains of fungi belonging to other thraustochytrid fungi, such as those with the American Type Culture Collection, ATCC Numbers 18906, 18907, 20890, 20891, 20892, 26185 belonging to Thraustochytrium sp., No. 28210 belonging to *Thraustochytrium roseum* Gaertner and No. 34304 belonging to *Thraustochytrium aureum* Goldstein may also be used. A suitable medium for example, is one containing peptone, yeast extract, glucose and sea water. Any other medium that supports good growth of the fungus also may be used. The culture is grown for 2 days at a room temperature ranging from 25 to 30° C. This culture is used as the inoculum and used to inoculate a medium with enhanced viscosity. The compound that is added to increase viscosity may be one of the common polymers, such as dextran or polyvinyl pyrrolidone (PVP) that are not utilised as nutrients by the organisms, but only contribute to increasing the medium viscosity. For example, polyvinyl pyrrolidone (PVP) is a water-soluble polymer of basic nature (McGraw-Hill Encyclopaedia of Science and Technology, Vol. 10, 1982). PVP is commonly used to increase fluid viscosity and is a suitable agent for this purpose (Podolsky, R. D. and R. B. Emlet, 1993. Journal of experimental biology 176: 207–221). In the present example, PVP at concentrations of 0.1 to 1.0% are added to the medium. Cultures may be grown in flasks on a rotary shaker in the laboratory or in a fermentor when large scale cultivation is required. The culture is allowed to grow at room temperature of 25 to 30° C. or any temperature at which the particular strain grows best. After a suitable period, for example 2 to 7 days growth, cells from the culture are harvested. This may be done by any appropriate method, such as centrifugation, continuous flow centrifugation, filtration etc. Cells thus obtained may be used for all applications that require thraustochytrid cells. Such use may include cell biomass for animal feed, human food supplement or extraction of pure DHA and EPA.

The present invention thus relates to a process to enhance the levels of the omega-3 PUFAs, DHA and EPA. By this process, strains of cultures of thraustochytrids can be made to produce higher levels of these PUFAs than they do under other conditions. Besides, even strains that contain only moderate quantities of these PUFAs under normal conditions can be made to produce greater amounts within their cells.

The invention is described in detail hereafter with reference to the accompanying drawings, which are provided merely to illustrate the invention.

BRIEF DESCRIPTION OF THE ACCOMPANYING DRAWINGS

The following examples are given by way of illustrations of the present invention and therefore, should not be construed to limit the scope of the present invention.

EXAMPLE—1

Figure 1:
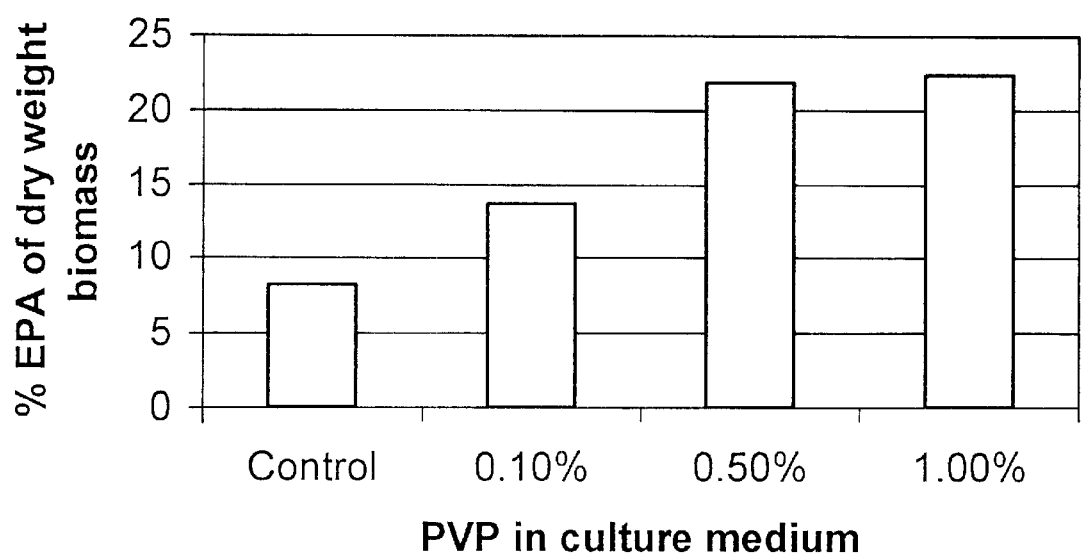
FIG. 1 represents the EPA contents of a thraustochytrid strain NIO-TH 21, corresponding in its morphology and life cycle to the species *Ulkenia radiata* Gaertner, being the culture with Accession No. AB22115 of the National Institute of Bioscience and Human-Technology, Japan, when grown in a liquid nutrient culture medium.
Figure 2:
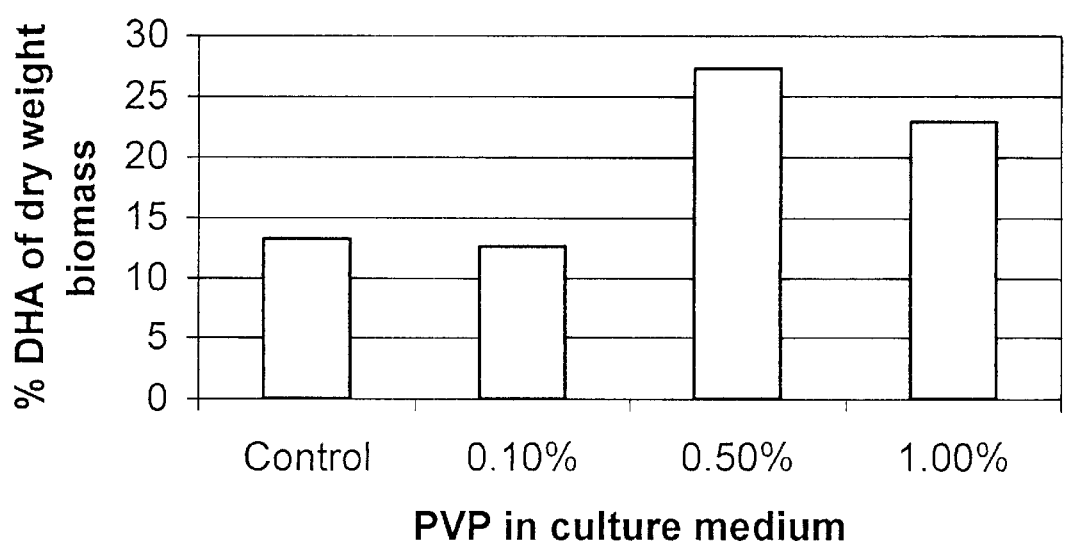
FIG. 2 represents the DHA contents of a thraustochytrid strain NIO-TH 21, corresponding in its morphology and life cycle to the species *Ulkenia radiata* Gaertner, being the culture with Accession No. AB22115 of the National Institute of Bioscience and Human-Technology, Japan, when grown in a liquid nutrient culture medium.

A culture of a thraustochytrid, belonging to strain #NIO-TH 21 was inoculated into 100 ml of a culture medium containing: gelatin peptone—1.5% Wt.; Yeast extract—0.1% Wt.; Glucose—1.0% Wt. and Sea water—100 ml. The cultures were grown for 2 days on a shaker at room temperature of 25–30° C. These cultures were used as innoculum for the experiment. Three sets of cultures were set up using a medium with the same composition as above. The first set contained an addition of 0.1% polyvinyl pyrrolidone. The second set contained 0.5% PVP, while the third contained 1.0% PVP. The experiment was carried out by adding 10 ml of the innoculum into 100 ml of the culture medium for each set. The cultures were grown for 3 days on a shaker at room temperature of 25–30° C. At the end of this period, cells were harvested by centrifugation, fatty acids extracted and analyzed by gas chromatography. Cultures grown in media with increased viscosity by adding PVP contained nearly 0.5 to 2 times more EPA than those grown in a medium without increased PVP (FIG. 1).

EXAMPLE—2

A culture of a thraustochytrid, belonging to strain #NIO-TH21 was inoculated into 100 ml of a culture medium containing: gelatin peptone—1.5% Wt.; Yeast extract—0.1% Wt.; Glucose—1.0% Wt. and sea water—100 ml. The cultures were grown for 2 days on a shaker at room temperature of 25–30° C. These cultures were used as innoculum for the experiment. Three sets of cultures were set up using a medium with the same composition as above. The first set contained an addition of 0.1% polyvinyl pyrrolidone. The second set contained 0.5% PVP, while the third contained 1.0% PVP. The experiment was carried out by adding 10 ml of the innoculum into 100 ml of the culture medium for each set. The cultures were grown for 3 days on a shaker at room temperature of 25–30° C. At the end of this period, cells were harvested by centrifugation, fatty acids extracted and analyzed by gas chromatography. Cultures grown in media with increased viscosity by adding 0.5 and 1.0% PVP contained nearly 2 times more DHA than those grown in a medium without PVP (FIG. 1).

The main advantages of the present invention are:
1. The DHA and EPA levels of thraustochytrids normally present in cultures can be further enhanced.
2. Even those strains that have only moderate quantities of DHA and EPA can be enriched in these fatty acids.
3. The viscosity of the medium is increased by addition of polyvinyl pyrrolidone, an easily available chemical.
4. Polyvinyl pyrrolidone is not used as nutrition by the cultures and, therefore, does not interfere with their normal metabolism.
5. Polyvinyl pyrrolidone is not toxic to the cultures and does not harm their normal metabolism.

We claim:
1. A method for enhancing levels of docosahexaenoic acid and eicosapentaenoic acid in thraustochytrid fungi, comprising the steps of: (a) culturing the thraustochytrid fungal strain *Ulkenia radiata* Gaertner deposited at the National Institute of Bioscience & Human Technology, Japan and bearing Accession No. AB22115, in a culture medium for 2 to 5 days at 25° C. to 30° C.; (b) inoculating a medium containing 0.1 to 1% polyvinyl pyrrolidone with the thraustochytrid fungal strain of step (a) and culturing it for 3 days at 25° C. to 30° C.; and (c) harvesting the cells by centrifugation and extracting the enhanced amounts of docosahexaenoic acid and eicosapentaenoic acids from the cells.

2. A method as claimed in claim 1 wherein the culture medium used comprises peptone in the range of 0.5% Wt. to 1.5% Wt.; yeast extract in the range of 0.01% Wt. to 0.1% Wt.; glucose in the range of 0.01% to 1.0% Wt.; and sea water of 100 ml.

3. A method as claimed in claim 2, wherein the culture comprises 1.5% peptone; 0.1% yeast extract; 1.0% glucose; 0.5% polyvinyl pyrrolidone and 100 ml sea water.

4. A method according to claim 2, wherein said culture medium comprises 1.5% peptone.

5. A method according to claim 2, wherein said culture medium comprises 0.1% yeast extract.

6. A method according to claim 2, wherein said culture medium comprises 1.0% glucose.

* * * * *